United States Patent [19]

Juichi et al.

[11] 4,113,782
[45] Sep. 12, 1978

[54] PROCESS FOR THE PREPARATION OF FORMYLATED PHENOXY COMPOUNDS

[75] Inventors: Imamura Juichi, Chofu; Takehara Masahiko, Chigasaki; Kizawa Kazuhiro, Kanagawa, all of Japan

[73] Assignee: Agency of Industrial Science and Technology, Tokyo, Japan

[21] Appl. No.: 657,887

[22] Filed: Feb. 13, 1976

[30] Foreign Application Priority Data

Feb. 18, 1975 [JP] Japan .................................. 50-19458

[51] Int. Cl.² ............................................. C07C 45/00
[52] U.S. Cl. .................................... 260/600 R; 560/53
[58] Field of Search ........... 260/524 R, 600 R, 521 B; 560/53

[56] References Cited

U.S. PATENT DOCUMENTS

| | | | |
|---|---|---|---|
| 1,380,277 | 5/1921 | Weiss et al. | 260/600 R |
| 2,245,528 | 6/1941 | Loder | 260/524 R |
| 2,785,199 | 3/1957 | Himel | 260/524 R |
| 2,959,613 | 11/1960 | Whitfield | 260/521 B X |
| 3,910,996 | 10/1975 | Onopchenko et al. | 260/599 |

*Primary Examiner*—Bernard Helfin

[57] ABSTRACT

A process for the preparation of formylated phenoxy compounds characterized in that a methylated phenoxy compound such as p-methoxytoluene in oxidized in liquid phase under heating with pressurized gaseous oxygen in the presence of at least one of lower fatty acids and anhydrides thereof and by the aid of at least one of soluble salts of metals selected from the group consisting of cobalt, manganese, chromium and nickel, as catalyst.

14 Claims, No Drawings

PROCESS FOR THE PREPARATION OF FORMYLATED PHENOXY COMPOUNDS

BACKGROUND OF THE INVENTION

The present invention relates to a process for the preparation of formylated phenoxy compounds. More particularly, the present invention relates to a process for converting methyl group in a methylated phenoxy compound selectively into formyl group by liquid phase oxidation with molecular oxygen. Formylated phenoxy compounds are useful as perfumes, medicaments and starting materials for other fine chemicals.

It is publicly known that when a methylated aromatic compound is oxidized with molecular oxygen in liquid phase in the presence of a Redox catalyst, the methyl group of the aromatic compound is converted by oxidation into carboxyl group via formyl group. In this oxidation process, however, the rate of oxidizing formyl group to carboxyl group is much faster than that of oxidizing methyl group to formyl group. Thus, the production of formyl (aldehyde) compounds in a good yield is extremely difficult according to this oxidation process. For this reason, there has not yet been proposed an industrially operable process for preparing formylated aromatic compounds in a good yield by oxidizing methylated aromatic compounds with molecular oxygen.

BRIEF SUMMARY OF THE INVENTION

Accordingly, it is a primary object of the present invention to provide an industrially operable process for the preparation of formylated aromatic compounds in a good yield wherein methylated aromatic compounds are oxidized with molecular oxygen.

It is another object of the present invention to provide an industrially operable process for the production of formylated phenoxy compounds wherein methylated phenoxy compounds are oxidized in liquid phase under heating with pressurized oxygen-containing gas to produce the formylated phenoxy compounds selectively.

It is still another object of the present invention to provide a process for oxidizing methylated phenoxy compounds with molecular oxygen to convert the methyl group selectively into formyl group.

Other and further objects, features and advantages of this invention will become more fully apparent from the following description.

DETAILED DESCRIPTION OF THE INVENTION

As a result of many researches made to develop a process for oxidizing methylated aromatic compounds with molecular oxygen to convert the methyl group into formyl group, it has now been found that when methylated benzene compounds introduced thereinto an alkoxy or aryloxy group are oxidized with pressurized oxygen under specific reaction conditions, the methyl group of the benzene compounds is selectively oxidized to formyl group to afford aromatic aldehydes in a good yield.

In accordance with the present invention, there is provided a process for the preparation of formylated phenoxy compounds characterized in that a methylated phenoxy compoud is oxidized in liquid phase under heating with pressurized oxygen-containing gas in the presence of at least one reaction solvent selected from the group consisting of lower fatty acids and anhydrides thereof and by the aid of a catalyst which is at least one soluble salt of metals selected from the group consisting of cobalt, manganese, chromium and nickel, thereby selectively converting the methyl group of the phenoxy compound into formyl group.

In the present invention, at least one lower fatty acid and/or at least one anhydride thereof functioning as both reaction promotor and reaction solvent is added to the reaction system. The term "lower fatty acid" is used herein to mean an aliphatic carboxylic acid with 1-8 carbon atoms. Preferable examples of the lower fatty acid include acetic acid, propionic acid, n-butyric acid and isobutyric acid. Especially preferable reaction solvents in practice of the present invention are acetic acid and acetic anhydride. Halogenated lower fatty acids, i.e. lower fatty acids substituted by halogen such as chlorine or bromine are also included in the category of the lower fatty acids utilizable for the present invention. However, the use of such halogenated lower fatty acids is less recommendable because of their cost and difficulty in handling. In the present invention, a reaction solvent utilizable for conventional oxidative reactions may be used in addition to the lower fatty acid or an anhydride thereof. Preferable examples of such reaction solvent include aromatic hydrocarbons such as benzene and toluene and the corresponding halogenated derivatives. Besides these, any organic solvent can be used so far as it is inert to the oxidation reaction. The organic solvent which is inert to the oxidation reaction and can replace a part of the reaction solvent is used in an amount of at most 80% by weight based on the total reaction solvents.

The catalyst used in the present invention is one or more soluble salts of metals selected from the group consisting of cobalt, manganese, chromium and nickel. In the reaction solvent, such metal salt produces the relevant metal ion which is then coordinated with the lower fatty acid or an anhydride thereof and functions as an effective catalyst for synthetizing aldehydes. In the present invention, any of the soluble salts of the metals can be used so far as it is soluble in the solvent and capable of producing in the reaction liquid the relevant metal ion containing the lower fatty acid or an anhydride thereof as ligand. For example, naphthenates, acetylacetonates and lower fatty acid salts of the above mentioned metals are preferably used in the present invention. Especially preferable catalysts are acetates of these metals.

The reactivity and selectivity of the catalyst used in the present invention varies considerably according to the sort of metal ions. A metal ingredient most excellent in both activity and selectivity is cobalt and the catalytic effect is decreased in the written order of manganese, nickel and chromium. In the metal ion, the relation between activity and selectivity is still unclear but generally selectivity of the catalyst becomes higher as its activity becomes higher. Thus, the extent of the applicable reaction conditions becomes broader as the activity of the catalyst becomes higher.

The amount of at least one lower fatty acid and/or at least one anhydride thereof used in the present invention varies considerably according to the sort of the catalyst used and somewhat according to the sort of the lower fatty acid itself. Generally, however, the lower fatty acid ingredient is used in an amount of 0.3–18 molar proportion, preferably 7–15 molar proportion to the starting compound. In case the lower fatty acid anhydride is used, its molar proportion is converted on the fatty acid basis. Actually, therefore, the molar proportion of the lower fatty acid anhydride is ½ of the nominal molar proportion calculated as the fatty acid. If the amount of this reaction solvent used is too small, both the oxidation rate of the starting material and the rate of selection to aldehyde are lowered, and in the extreme case, the reaction itself will not proceed under the reaction conditions adopted. On the other hand, if the amount of the reaction solvent used is excessive, no reduction is noted in the rate of selection to aldehydes but the concentration of the starting material is decreased so that the reaction rate is reduced and the efficiency per unit volume becomes poor. Thus, the use of an excessively large amount of the reaction solvent is not recommended.

The amount of the metal salt varies significantly according to the sort of the metal used and somewhat according to other reaction conditions. In the case of the cobalt salt, for example, its amount is about 0.0001-1.0 molar proportion to the solvent. However, addition of a relatively large amount of the lower fatty acid and addition of the cobalt salt in an amount of 0.005-0.1 molar proportion to the solvent are recommended to obtain the aldehyde especially in a better yield. In case a salt of manganese, nickel or chromium is used as catalyst, addition of the metal salt in an amount as small as 0.0001 molar proportion to the solvent permits the formation of the desired aldehyde. In this case, however, the yield of the aldehyde is considerably low as compared with the case of using the cobalt salt. Thus, addition of these metal salts in an amount of 0.0005-0.5 molar proportion, preferably 0.01-0.05 molar proportion to the solvent is desirable to synthetize aldehydes in a good yield. If the amount of the catalyst used is too small, the reaction rate and the selectivity are both reduced. The reaction no longer proceeds in the absence of the catalyst. On the other hand, the reaction is not disturbed if the catalyst is added excessively. As the reaction proceeds in a homogeneous system, however, addition of an excessively large amount of the catalyst to such a degree that the catalyst remains undissolved in the reaction liquid is meaningless. Existence of a large amount of insoluble matters in the reaction system rather induces a minus effect such that the fluidity of the reaction liquid is reduced.

The optimum reaction temperature and partial pressure of oxygen vary according to the reaction conditions such as the sorts and amounts of the catalyst and the solvent and the sort of the starting material used. In a batch reaction system, a reaction temperature within a range of 100°-230° C., preferably 120°-190° C. and a partial pressure of oxygen within a range of 2-100 kg/cm², preferably 10-70 kg/cm² are preferred to enhance the yield of aldehydes satisfactorily. In the case of a continuous reaction system, the optimum reaction temperature is somewhat raised to a range of 100°-250° C., preferably 130°-220° C. Even in the case of using a partial pressure of oxygen as low as 2-10 kg/cm², aldehydes can be obtained in a high rate of selectivity by suitably controlling other reaction conditions. The reaction temperature and the partial pressure of oxygen vary according to other reaction conditions and are not necessarily limited to the above defined ranges. When a soluble salt of manganese, nickel or chromium which is lower in catalytic activity than cobalt salts is used as catalyst, the reaction temperature has to be elevated to a range somewhat higher than that in the case of using a cobalt salt.

In addition to oxygen itself, various oxygen-containing gas such as air and a mixture of air and oxygen can be used as the oxidizing agent in the present invention. However, the use of oxygen is suitable, considering the fact that the reaction is desirably carried out at a relatively high partial pressure of oxygen.

The oxidation process according to the present invention is applied to synthesis of aromatic aldehydes from mono- or poly-methylated phenoxy compounds. The starting materials used for the process of the present invention are represented by the following general formula:

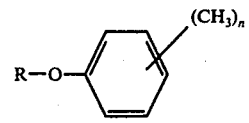

wherein R stands for a hydrocarbyl group selected from the group consisting of alkyl, cycloalkyl, aryl and aralkyl groups which may be substituted by one or more substituents inert to the oxidation reaction and $n$ is an integer of 1-5.

The hydrocarbyl group R has 1-20 carbon atoms in its molecule. Illustrative of the hydrocarbyl group are alkyl groups such as methyl, ethyl, n-propyl, isopropyl, n-hexyl, n-octyl and isooctyl groups; cycloalkyl groups such as cyclohexyl, cyclooctyl, methylcyclohexyl and ethylcyclohexyl groups; aryl groups such as phenyl, tolyl, xylyl, ethylphenyl, n-propylphenyl, isopropylphenyl, butylphenyl and naphthyl groups and aralkyl groups such as benzyl and phenethyl groups.

In the present invention, these hydrocarbyl groups may be substituted by one or more inert substituents which give no trouble to the oxidation reaction. Illustrative of the inert substituents in this case are hydrocarbyloxy groups with 1-10 carbon atoms such as methoxy, ethoxy, n-propoxy, isopropoxy, n-butoxy, n-octyloxy, cyclohexyloxy and similar cycloalkyloxy, phenoxy and benzyloxy groups; hydrocarbyloxycarbonyl groups such as methoxycarbonyl, ethoxycarbonyl, n-propoxycarbonyl, isopropoxycarbonyl, n-butoxycarbonyl and n-octyloxycarbonyl groups; and halogen atoms such as chlorine and bromine atoms. These inert substituents may further be substituted by a similar inert substituent or substituents. Hydrocarbyl groups substituted by one or more reactive substituents such as hydroxyl, mercapto and amino groups which disturb the oxidation reaction are inappropriate as the hydrocarbyl group R. The free hydroxyl or mercapto group processes auto-oxidation-inhibiting action and strongly inhibits proceeding of the oxidation reaction of the present invention. As a tertiary carbon atom is more easily oxidized than methyl group, existence of such tertiary carbon atom may disturb selectivity in the reaction. For example, if a tertiary carbon atom is present in the substituent R in the starting phenoxy compound of the above general formula having a methyl group in the meta-position of the benzene ring which is intended to be converted into formyl group and is less reactive than the tertiary carbon atom, the rate of selection to the aldehyde product in the oxidation reaction is seriously reduced. However, existence of such tertiary carbon atom gives no trouble if a methyl group in the para-position of the benzene ring, which is more reactive, is oxidized.

In the ring-methylated phenoxy compounds used in the present invention as starting material, two or more methyl groups may be present in the benzene nucleus. In this case, however, these methyl groups tend to be oxidized in the written order of para-, ortho- and meta-positions to the substituent R—O—. Thus, the staring phenoxy compounds carrying methyl group in the para-position of their benzene nucleus are selectively oxidized in the p-methyl group to form p-formylphenoxy products. Similarly, the starting materials carrying no methyl group in the para-position of their benzene nucleus but carrying two methyl groups in the ortho- and meta-positions are oxidized preferentially in the ortho-methyl group to form o-formyl-m-methyl products predominantly. According to the present invention, monoformyl products can be prepared in a high yield and in a high rate of selection from methylated phenoxy starting materials carrying at least two methyl groups in their benzene nucleus by suitably controlling the reaction conditions. Although diformyl products may also be prepared from the dimethyl or trimethyl starting materials, the yield and the rate of selection in this case are so bad that there is brought about no industrially technical merit. This is due to the reason that the formyl group formed at first by oxidation of one methyl group is more easily oxidizable than the remaining methyl group or groups and thus is oxidized to carboxyl group prior to oxidation of the remaining methyl group or groups to formyl group or groups. Accordingly, the present invention is advantageously applied to the preparation of monoformyl products in an industrial scale from the starting materials carrying plural methyl groups by suitably controlling the reaction time.

Examples of the methylated phenoxy compounds used as starting materials for the process of this invention include tolyloxmethane (or methoxytoluene), tolyloxyethane (or ethoxytoluene), tolyloxy-n-propane (or n-propoxytoluene), tolyloxyisopropane (or isopropoxytoluene), tolyloxy-n-butane (or-n-butoxytoluene), tolyloxy-isobutane (or isobutoxytoluene), tolyloxycyclohexane (or cyclohexyloxytoluene), tolyloxymethylcyclohexane (or methylcyclohexyloxytoluene), tolyloxybenzene (or phenoxytoluene), tolyloxytoluene (or ditolyl ether), xyloxymethane (or methoxyxylene), xyloxyethane (or ethoxyxylene), xyloxy-n-propane (or n-propoxyxylene), xyloxyisopropane (or isopropoxyxylene), xyloxy-n-butane (or n-butoxyxylene), xyloxycyclohexane (or cyclohexyloxyxylene), xyloxybenzene (or phenoxyxylene), xyloxytoluene (or tolyloxyxylene), mesityloxymethane (or methoxymesitylene), mesityloxyethane (or ethoxymesitylene), mesityloxy-n-propane (or n-propoxymesitylene), mesityloxy-n-butane (or n-butoxymesitylene), mesityloxycyclohexane (or cyclohexyloxymesitylene), mesityloxybenzene (or phenoxymesitylene), mesityloxytoluene (or tolyloxymesitylene), methoxyphenyl tolyl ether, phenoxyphenyl tolyl ether, methoxycarbonylphenyl tolyl ether, methoxyethyl tolyl ether and methoxycarbonylethyl tolyl ether.

The process of the present invention can be carried out batchwise or continuously but the latter continuous process wherein control of the reaction temperature is easy is desirable in view of the fact that the reaction is preparably completed within a short period of time to synthetize the aldehyde product in a good yield and that the oxidation reaction itself is highly exothermic and an excessively higher reaction temperature induces reduction of the rate of selection to the aldehyde product.

Separation and recovery of the prepared aldehyde product, catalyst, solvent and unreacted starting materials from the reaction mixture are attained by methods well known to those skilled in the art. For example, the aldehyde product can be obtained easily in a high yield by removing the lower fatty acid in the reaction mixture by distillation under reduced pressure, adding a solvent such as toluene to the distillation residue, subjecting the mixture to centrifugal separation under cooling thereby removing the catalyst and then distilling the residual liquid under reduced pressure.

The present invention will now be explained in more detail by way of examples but it is to be construed that scope of the invention is not limited to these examples.

EXAMPLE 1

In a 300 ml SUS-32 stainless steel autoclave equipped with a stirrer, a thermometer and a gas inlet were placed 30 g of p-methoxytoluene, 184 g of acetic acid and 12.0 g of cobalt acetate tetrahydrate. The liquid mixture was maintained at 90°–120° C. while vigorously stirring the mixture. From a pressure tank, gaseous oxygen was introduced into the autoclave through a pressure regulator and the pressure of oxygen was kept at 60 kg/cm$^2$. As soon as the gaseous oxygen was introduced, a violent oxidation reaction took place so that it was difficult to maintain the reaction temperature at a definite temperature range. However, careful attention was paid to maintain the reaction temperature as definite as possible and the quantity of oxygen consumed was roughly calculated from decrease in the pressure of oxygen in the oxygen pressure tank. At the time an almost required quantity of oxygen was absorbed, the reactor was quickly cooled to stop the reaction. The reaction product was analyzed according to gas chromatography. A result of the experiments was as shown in Table 1. A column material used for the gas chromatography was silane-treated Celite 545 on which 10% by weight of Silicone oil OV-17 had been carried. This method for analysis was common to all of the examples. The method for oxidation reaction in the following examples was quite identical with that adopted in this example except Example 14 where a flow system was adopted.

Table 1

| Exp. No. | Reaction temperature (° C) | Reaction time (min) | Reaction rate of p-methoxytoluene (%) | Rate of selection to p-methoxybenzaldehyde (mol %) |
|---|---|---|---|---|
| 1 | 115–126 | 2.8 | 89.8 | 71.2 |
| 2 | 115–145 | 2.1 | 51.8 | 70.2 |
| 3* | 120–134 | 3.5 | 98.6 | 35.3 |
| 4 | 91–98 | 8.0 | 18.9 | 47.8 |

*In this experiment, the reaction proceeded excessively so that the rate of selection to p-methoxybenzaldehyde was reduced.

EXAMPLE 2

In the reaction apparatus described in Example 1 were placed 70 g of p-methoxytoluene, 172 g of acetic acid and 14.0 g of cobalt acetate tetrahydrate. The oxidation reaction was carried out in the same manner as described in Example 1. As the purpose of this example was to investigate any influence of the pressure of oxygen, the reaction temperature was planned to be kept at 150° C. Actually, however, the temperature could not entirely be kept at 150° C. on account of a violent exothermic reaction so that the maximum temperature reached up to about 165° C. A result of the experiments was as shown in Table 2.

Table 2

| Exp. No. | Pressure of oxygen (kg/cm² gauge) | Reaction time (min) | Reaction rate of p-methoxy-toluene (%) | Rate of selection to p-methoxybenzaldehyde (mol %) |
|---|---|---|---|---|
| 1 | 15 | 60 | 58 | 56 |
| 2 | 30 | 12.0 | 58 | 67 |
| 3 | 45 | 6.5 | 56 | 70 |
| 4 | 60 | 4.0 | 66 | 73 |
| 5 | 90 | 1.0 | 53 | 71 |

EXAMPLE 3

In the reaction apparatus described in Example 1 were placed 70 g of p-methoxytoluene, 172 g of acetic acid and cobalt acetate tetrahydrate in an amount of 0.01–0.5 molar proportion to the p-methoxytoluene. The oxidation reaction was carried out in the same manner as described in Example 1 to investigate any influence of the concentrations of the catalyst. The pressure of oxygen was 15 kg/cm² (gauge) and the reaction temperature was kept at 150° C. (Actually, however, the maximum reaction temperature temporarily reached up to about 165° C.) A result of the experiments was as shown in Table 3.

Table 3

| Exp. No. | X/Y* (molar ratio) | Reaction time (min) | Reaction rate of p-methoxytoluene (%) | Rate of selection to p-methoxybenzaldehyde (mol %) |
|---|---|---|---|---|
| 1 | 0.01 | 28 | 54 | 43 |
| 2 | 0.05 | 32 | 64 | 56 |
| 3 | 0.1 | 61 | 83 | 51 |
| 4** | 0.1 | 53 | 67 | 55 |
| 5 | 0.2 | 90 | 72 | 45 |
| 6 | 0.5 | 279 | 60 | 38 |

*X = Cobalt acetate tetrahydrate $Co(CH_3CO_2)_2 \cdot 4H_2O$  Y = p-Methoxytoluene $H_3C \cdot C_6H_4 \cdot O(CH_3)$ (p-position)
**The operation was conducted under pressure of 10 kg/cm² (gauge, oxygen).

EXAMPLE 4

In this example, any influence of the concentrations of catalyst in the case of changing the mixing ratio of p-methoxytoluene to acetic acid was investigated. In the same reaction apparatus as described in Example 1 were placed 70 g of p-methoxytoluene, 60 g of acetic acid and a given amount of cobalt acetate tetrahydrate. The reaction was carried out in a similar manner to that described in Example 3. After reacting the mixture for 2 hours, the product was subjected to analysis whereby a result as shown in Table 4 was obtained.

Table 4

| Exp. No. | X/Y (molar ratio) | Reaction rate of p-methoxytoluene (%) | Rate of selection to p-methoxybenzaldehyde (mol %) |
|---|---|---|---|
| 1 | 0.001 | 13 | 36 |
| 2 | 0.005 | 44 | 36 |
| 3 | 0.01 | 52 | 41 |
| 4 | 0.05 | 54 | 50 |
| 5 | 0.077 | 59 | 45 |
| 6* | 0.1 | 55 | 46 |
| 7* | 0.2 | 43 | 47 |

*In these experiments, the catalyst not entirely dissolved in the reaction liquid.

EXAMPLE 5

In the reaction apparatus described in Example 1 were placed 70 g of p-methoxytoluene, 21 g of acetic acid and 14.0 g of cobalt acetate tetrahydrate. The mixture was reacted for 2 hours at various reaction temperatures while maintaining the pressure of oxygen at 15 kg/cm². On account of a violent exothermic reaction, the maximum reaction temperature became 10°–15° C. higher than the predetermined point. A result of the experiments is shown in Table 5.

Table 5

| Exp. No. | Reaction temperature (° C) Pre-determined value | Reaction temperature (° C) Maximum value | Reaction rate of p-methoxytoluene (%) | Rate of selection to p-methoxybenzaldehyde (mol %) |
|---|---|---|---|---|
| 1 | 100 | 105 | 12 | 46 |
| 2 | 125 | 140 | 69 | 46 |
| 3 | 150 | 160 | 40 | 68 |
| 4 | 180 | 195 | 25 | 34 |
| 5 | 200 | 215 | 23 | 28 |

EXAMPLE 6

In the same reaction apparatus as described in Example 1 were placed 30 g of p-methoxytoluene, 12.0 g of cobalt acetate tetrahydrate and various kinds of solvent in an amount of 10 molar proportion to the p-methoxytoluene used. The reaction was conducted under pressure of oxygen kept at 60 kg/cm² and at a reaction temperature of 130° C. (Actually, however, the maximum temperature reached up to about 145° C.) whereby a result as shown in Table 6 was obtained. In case a mixture of solvents was used, the total amount of the solvents was adjusted to 10 molar proportion to the p-methoxytoluene used. In the case of using acetic anhydride, its amount was calculated in terms of acetic acid. In other words, when acetic anhydride was used alone, its amount was 5 molar proportion to the p-methoxytoluene used.

Table 6

| Exp. No. | Sort of solvent (Numerals standing for molar ratio) | Reaction time (min) | Reaction rate of p-methoxytoluene (%) | Rate of selection to p-methoxybenzaldehyde (mol %) |
|---|---|---|---|---|
| 1 | Acetic acid | 2.7 | 75.3 | 72.2 |
| 2* | Acetic anhydride | 3.0 | 92.9** | 47.2 |
| 3 | Butyric acid | 2.8 | 78.2 | 43.5 |
| 4 | Propionic acid + Acetic acid (1:1) | 2.7 | 77.1 | 49.2 |
| 5 | Propionic acid + Isobutyric acid + Butyric acid (2:1:2) | 3.1 | 69.1 | 39.8 |
| 6 | Acetic acid + Acetic anhydride (1:1) | 2.8 | 79.1 | 70.1 |
| 7* | Monochloroacetic acid | 3.0 | 43.0 | 33.7 |
| 8*** | Acetic acid | 11.0 | 50.3 | 58.3 |

*These experiments were conducted under pressure of oxygen kept at 50 kg/cm² and at a reaction temperature of 150° C.
**In this experiment, the reaction proceeded excessively so that the rate of selection to p-methoxybenzaldehyde was reduced.
***This experiment was conducted under pressure of oxygen kept at 5 kg/cm².

EXAMPLE 7

In the same reaction apparatus as described in Example 1 were placed 30 g of p-methoxytoluene, a given amount of a solvent and a given concentration of a cobalt salt catalyst. The oxidation reaction was carried out under pressure of oxygen kept at 50 kg/cm$^2$ and at a reaction temperature of 130° C. whereby a result as shown in Table 7 was obtained. Table 7 also shows as Comparative Examples the data obtained in the case of the lower fatty acid or an anhydride thereof being absent. As is evident from the table, absence of the lower fatty acid or an anhydride thereof causes serious reduction of the yield of p-methoxybenzaldehyde.

Table 7

| Exp. No. | Solvent*[1] | Catalyst*[1] | Reaction time (min) | Reaction rate of p-methoxytoluene (%) | Rate of selection to p-methoxybenzaldehyde (mol %) |
|---|---|---|---|---|---|
| 1 | Acetic acid(5)+Benzene(7.5) | Co(OAc)$_2$*[2] (0.2) | 2.0 | 76.4 | 29.2 |
| 2 | Acetic acid(3.5)+Benxene(9) | Co(OAc)$_2$ (0.14)+Co-N*[3](0.06) | 18.5 | 24.4 | 39.7 |
| 3 | Acetic acid(3.5)+Chloro.benzene | Co(OAc)$_2$*[2] (0.14)+Co-N*[3](0.06) | 23.0 | 44.2 | 47.4 |
| [Comparative Examples] | | | | | |
| 4 | Benzene(10) | Co-N*[3] | 150 | 8.0 | 10.0 |
| 5 | Benzene(10) | Cobalt acetylacetonate (0.2) | 18.0 | 13.9 | 18.2 |

*[1] The parenthesized numerals stand for an amount of the added solvent or catalyst in terms of a molar proportion to the starting p-methoxytoluene.
*[2] Cobalt acetate tetrahydrate.
*[3] Cobalt naphthenate

EXAMPLE 8

In the reaction apparatus described in Example 1 were placed 30 g of p-methoxytoluene, 184 g of acetic acid and an acetate of various kinds of metal in an amount of 0.2 molar proportion to the p-methoxytoluene. The oxidation reaction was conducted under pressure of oxygen kept at 50 kg/cm$^2$ and at a reaction temperature of 150° C. whereby a result as shown in Table 8 was obtained.

Table 8

| Exp. No. | Metal | Reaction time (min.) | Reaction rate of p-methoxytoluene (%) | Rate of selection to p-methoxybenzaldehyde (mol %) |
|---|---|---|---|---|
| 1 | Manganese | 28 | 55.2 | 49.3 |
| 2 | Nickel | 55 | 54.9 | 23.6 |
| 3 | Chromium | 50 | 12.3 | 54.8 |
| 4* | Manganese | 8 | 44.8 | 29.1 |
| 5** | Nickel | 31 | 57.3 | 20.0 |

*In this experiment, 209 g of acetic anhydride was used in place of acetic acid while the amount of p-methoxytoluene was decreased to 20 g.
**In this experiment, a mixture of 59 g of acetic anhydride and 92 g of acetic acid was used in place of acetic acid.

EXAMPLE 9

Oxidation of p-methoxytoluene was carried out, using acetic acid, acetic anhydride or a mixture of acetic acid and benzene as solvent and nickel acetate tetrahydrate [Ni(CH$_3$CO$_2$)$_2$.4H$_2$O], manganese acetate tetrahydrate [Mn(CH$_3$CO$_2$)$_2$.4H$_2$O] or chromium acetate monohydrate [Cr(CH$_3$CO$_2$)$_3$.H$_2$O] as catalyst. Using the same reaction apparatus as described in Example 1, and varying the molar proportions of the solvent and the catalyst to the starting p-methoxytoluene, a series of experiments were performed under the following predetermined reaction conditions:

| | |
|---|---|
| Volume of the reaction liquid | 200 cc |
| Pressure of oxygen | 50 kg/cm$^2$ |
| Reaction temperature | 160° C |

A result of the experiments is shown in Table 9.

TAble 9

| Exp. No. | Solvent | Catalyst | Reaction time (min) | Reaction rate of p-methoxytoluene (%) | Rate of selection to p-methoxybenzaldehyde (mol %) |
|---|---|---|---|---|---|
| 1 | Acetic acid (0.6) | Nickel (0.01) | 45 | 6.5 | 34.3 |
| 2 | Acetic acid (12.5) | Nickel (0.01) | 15.5 | 33 | 15.1 |
| 3 | Acetic acid (0.6) | Manganese (0.01) | 25 | 14.2 | 19.9 |
| 4 | Acetic acid (11.5) + Benzene (1) | Manganese (0.2) | 23.5 | 46.8 | 52.8 |
| 5 | Acetic acid (8.8) + Benzene (3.7) | Manganese (0.2) | 28 | 30.7 | 26.4 |
| 6 | Acetic acid (11) + Benzene (2) | Nickel (0.2) | 58 | 59.2 | 20.5 |
| 7 | Acetic acid | Chromium | 130 | 5.2 | 28.1 |

TAble 9-continued

| Exp. No. | Solvent | Catalyst | Reaction time (min) | Reaction rate of p-methoxy-toluene (%) | Rate of selection to p-methoxybenzal-dehyde (mol %) |
| --- | --- | --- | --- | --- | --- |
| 8 | Acetic anhydride (0.6) | (0.01) Chromium (0.01) | 30 | 21.5 | 16.6 |

*The parenthesized numerals stand for an amount of the added solvent or catalyst in terms of a molar proportion to the starting p-methoxytoluene.

EXAMPLE 10

Oxidation of p-methoxytoluene was carried out in the same manner as described in Example 1 except that a mixture of 100 g of acetic acid, 50 g of acetic anhydride and 30 g of propionic acid was used as solvent in place of acetic acid and that a mixture of 10.0 g of cobalt acetate tetrahydrate and 10.0 g of nickel acetate tetrahydrate was used as catalyst. Although the reaction was conducted at a reaction temperature of 120° C., the maximum temperature reached up to 130° C. on account of a violent exothermic reaction. After lapse of 2.3 minutes, the amount of absorbed oxygen reached to a required value. The reactor was then cooled rapidly and the liquid product was subjected to analysis whereby it was found that the reaction rate of p-methoxytoluene was 57.5% and the rate of selection to p-methoxybenzaldehyde was 62.3 mol %.

EXAMPLE 11

Except that a mixture of 3.0 g of manganese acetate tetrahydrate, 1.0 g of chromium acetate monohydrate and 1.0 g of nickel acetate tetrahydrate was used as catalyst in place of cobalt acetate tetrahydrate used in Example 1, oxidation of p-methoxytoluene was carried out in the same manner as described in Example 1 under pressure of oxygen kept at 40 kg/cm$^2$ and at a reaction temperature of 150° C. As a required amount of oxygen was absorbed after lapse of 17 minutes, the reactor was cooled rapidly and the reaction product was subjected to analysis whereby it was found that the reaction rate of p-methoxytoluene was 49.5% and the rate of selection to p-methoxybenzaldehyde was 39.1 mol %.

EXAMPLE 12

Except that o- or m-methoxytoluene was used in place of p-methoxytoluene in Example 1, the reaction was carried out in the same manner as described in Example 1 under pressure of oxygen kept at 50 kg/cm$^2$ and at a reaction temperature of 125° C. In the case of oxidation of o-methoxytoluene requiring a reaction time of 15.5 minutes, the reaction rate of o-methoxytoluene was 34.0% and the rate of selection to o-methoxybenzaldehyde was 56.7 mol %. In the case of oxidation of m-methoxytoluene requiring a reaction time of 25 minutes, the reaction rate of m-methoxytoluene was 22.8% and the rate of selection to m-methoxybenzaldehyde was 19.5 mol %. In the case of conducting the oxidation reaction of m-methoxytoluene at 150° C. for 4.5 minutes, the reaction rate thereof was 37.5% and the rate of selection to m-methoxybenzaldehyde was 35.1 mol %.

EXAMPLE 13

As a result of maintaining the reaction temperature at 125° C. for 2.5 minutes and using cobalt naphthenate as catalyst in Example 8, the reaction rate of p-methoxytoluene and the rate of selection to p-methoxybenzaldehyde were 37.7% and 64.0 mol %, respectively.

EXAMPLE 14

An oxidation reaction was operated with a SUS 32 stainless steel bubbling tower provided with a jacket of 10 mm in inner diameter and 1000 mm in height. From a reservoir dioctyl phthalate maintained at 130° C. was supplied and recycled through the jacket so as to maintain the reaction liquid at a definite temperature. A liquid mixture containing 40 g of p-methoxytoluene, 200 g of acetic acid and 8 g of cobalt acetate tetrahydrate was introduced into the bubbling tower from the lower portion thereof at a flow rate of 30 ml/minutes. On the other hand, oxygen was supplied at a flow rate of 900 ml/min. (calculated at NTP) through a perforated plate (50 holes with a diameter of 0.4 mm were uniformly distributed all over the plate) mounted to the lower portion of an inlet for the liquid starting material. The reaction pressure was maintained at 50 kg/cm$^2$ and the product discharged from the reactor was conveyed to a water-cooled gas separator where a gaseous phase was separated from a liquid phase. An analysis of the liquid phase showed that the reaction rate of p-methoxytoluene was 73% and the rate of selection to p-methoxybenzaldehyde was 79 mol %.

In case the liquid starting material was composed of 40 g of p-methoxytoluene, 150 g of acetic acid, 50 g of acetic anhydride, 4 g of cobalt acetate tetrahydrate and 4 g of manganese acetate tetrahydrate in this experiment, the reaction rate of p-methoxytoluene and the rate of selection to p-methoxybenzaldehyde were 21% and 50 mol %, respectively.

In case the oxidation reaction was conducted similarly with a liquid starting material composed of 40 g of p-methoxytoluene, 200 g of 10% by weight of aqueous acetic acid and 20 g of cobalt acetate tetrahydrate, the reaction rate of p-methoxytoluene and the rate of selection to p-methoxybenzaldehyde were 40% and 73 mol %, respectively.

EXAMPLE 15

To 1.5 mols of p-cresol were added 1 mol of KOH, 1 mol of various kinds of commercially available bromohydrocarbons and a very small amount of powdery copper. The mixture was well stirred and heated under reflux for 2-3 hours to synthesize a product of the general formula:

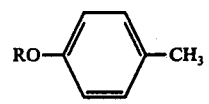

The product was thoroughly washed with an aqueous solution of alkali and then distilled under reduced pressure to prepare a starting material to be used for an oxidation reaction. The same reaction apparatus as described in Example 1 was charged with 30 g of a starting material of the above general formula and given amounts of acetic acid and cobalt acetate. An oxidation reaction of the starting material was carried out under pressure of oxygen maintained at 20 kg/cm² whereby a violent reaction took place after lapse of a definite induction period and the reaction temperature was rapidly elevated. The reaction product was subjected, as described in Example 1, to gas chromatography, a result of which is shown in Table 10. The reaction product was identified by a combination use of the GC-MS method and the NMR method.

uene according to the method described in Example 15. The resultant methyl-substituted diphenyl ethers were satisfactorily purified in a manner similar to that described in Example 15 and then subjected to oxidation reaction. A result of the experiments is shown in Table 11. The reaction products were isolated by topping the solvent from the reaction mixture under reduced pressure, extracting the residue with water and toluene, and then distilling the toluene layer under reduced pressure. In all of the experiments, the formation of dialdehydes Table 10

| Substituent R | Z/Y'*¹ (molar ratio) | X/Y'*¹ (molar ratio) | Reaction temperature (° C) | Induction period (sec.) | Reaction time (sec.) | Reaction rate (%) | Rate of selection to aldehyde (mol %) |
|---|---|---|---|---|---|---|---|
| $C_2H_5$*² | 10 | 0.3 | 155–192 | 0 | 25 | 74.8 | 65.9 |
| $C_2H_5$*² | 10 | 0.01 | 165–168 | 0 | 435 | 37.8 | 39.9 |
| iso-$C_3H_7$ | 10 | 0.3 | 158–178 | 0 | 65 | 71.0 | 50.0 |
| n-$C_4H_9$*³ | 10 | 0.3 | 170–193 | 0 | 50 | 90.3 | 37.3 |
| n-$C_7H_{15}$ | 13 | 0.1 | 161–193 | 0 | 68 | 65.1 | 49.5 |
| n-$C_9H_{19}$ | 13 | 0.05 | 155–179 | 0 | 113 | 75.2 | 43.7 |
|  | 10 | 0.3 | 185–198 | 0 | 35 | 24.0 | 77.0 |
| 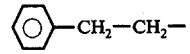 | 13 | 0.3 | 180–200 | 28 | 38 | 38.5 | 52.1 |
| 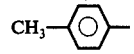 | 10 | 0.3 | 165–199 | 705 | 20 | 50.0 | 63.9 |
| 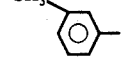 | 10 | 0.2 | 180–202 | 480 | 27 | 26.7 | 68.7 |
| 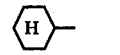 | 12.5 | 0.2 | 170–200 | 2840 | 20 | 61.9 | 56.1 |
| 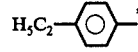 *⁴ | 12.5 | 0.2 | 180–200 | 20 | 100 | 61.1 | 31.5 |
| 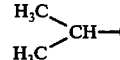 *⁴ | 10 | 0.3 | 130–162 | 120 | 80 | 54.6 | 14.9 |
| 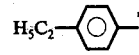 *⁵ | 15 | 0.3 | 155–177 | 0 | 90 | 67.9 | 16.8 |

*¹Z = Acetic
X = Co(CH₃CO₂)₂ · 4H₂O

Y' = RO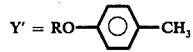CH₃

*²Prepared from diethyl sulfate and p-cresol according to the method described in Example 17.
*³Commercially available compound purified according to a usual manner.
*⁴Synthetized from p-bromotoluene and p-alkylphenol.
*⁵Synthetized from m-bromotoluene and p-ethylphenol
(Note:
Methyl group in this compound is present in meta-position,).

EXAMPLE 16

Methyl-substituted diphenyl ethers of the general formula:

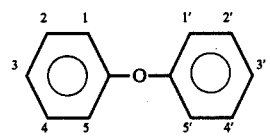

wherein the positions 1–5 and 1'–5 are occupied by H or CH₃ radical, were synthesized from commercially available methylphenols and bromobenzene or bromotolwere not detected. The methyl substituents in the starting materials were converted into formyl groups in the order of p-, o- and m-positions to the position of RO-substituent. Namely, the tendency of conversion was shown by the relation of p->o->m-position. For example, in the case of the starting material carrying methyl groups in o- and p-positions, the p-methyl group was preferentially oxidized to formyl group. Similarly, in the case of the starting material carrying methyl groups in o- and m-position, the o-methyl group was preferentially oxidized to formyl group. In Table 11, the grouping "CH₃CO" and the formula "H₂O" are shown simply by the notations "Ac" and "Aq", respectively.

Table 11

| Exp. No. | Position of Methyl substituent(s) in the starting compound | Solvent [amount used]* | Catalyst [amount used]* | Reaction temp. ° C | Pressure of oxygen (kg/cm²) | Induction period (sec) | Reaction time (sec.) | Reaction Rate (%) | Rate of Selection to aldehyde (mol %) |
|---|---|---|---|---|---|---|---|---|---|
| 11-1 | 3 | AcOH[5]+ (AcO)₂O[3] | (Co(AcO)₂ · 4Aq[0.1] | 185–196 | 20 | 0 | 70 | 30.8 | 29.4 |

Table 11-continued

| Exp. No. | Position of Methyl substituent(s) in the starting compound | Solvent [amount used]* | Catalyst [amount used]* | Reaction temp. °C | Pressure of oxygen (kg/cm²) | Induction period (sec) | Reaction time (sec) | Reaction Rate (%) | Rate of Selection to aldehyde (mol %) |
|---|---|---|---|---|---|---|---|---|---|
| 11-2 | 2, 3' | AcOH[5] + Propionic acid[2] + Benzene[7.5] | Co(AcO)₂ . 4Aq[0.2] (Ni(AcO)₂ . 4Aq[0.1] | 180–194 | 30 | 525 | 195 | 67.3 | 18.6 |
| 11-3 | 3, 3' | AcOH[12.5] | Mn(AcO)₂ . 4Aq[0.1] Ni(AcO)₂ . 4Aq[0.05] Cu(AcO)₂ . 1Aq[0.05] | 180–185 | 30 | 180 | 390 | 39.6 | 29.2 |
| 11-4 | 2 | AcOH[15] | Co(AcO)₂ . 4Aq[0.5] | 180–183 | 45 | 150 | 8 | 68.2 | 35.1 |
| 11-5 | 1, 3, 5 | AcOH[10] + (AcO)₂O[5] | Co(AcO)₂ . 4Aq[0.1] | 180–193 | 60 | 30 | 21 | 72.1 | 37.9 |
| 11-6 | 1, 2 | Butyric acid[13] | Co(AcO)₂ . 4Aq[0.2] Mn(AcO)₂ . 4Aq[0.2] | 180–185 | 40 | 135 | 40 | 58.3 | 31.5 |
| 11-7 | 1, 2, 3' | AcOH[10] | Co(AcO)₂ . 4Aq[0.3] | 155–191 | 40 | 0 | 35 | 71.5 | 61.8 |
| 11-8 | 2, 3, 2' | AcOH[5] + Chlorobenzene[5] + Toluene[3] | Co(AcO)₂ . 4Aq[0.2] | 180–195 | 60 | 611 | 137 | 49.1 | 25.3 |
| 11-9 | 1, 3, 5, 1' | AcOH[8] + (AcO)₂O[2] | Co(AcO)₂ . 4Aq[0.3] | 160–195 | 40 | 0 | 42 | 59.5 | 55.5 |

*In terms of molar proportion to the starting material used.

EXAMPLE 17

In 200 ml of water were dissolved 0.5 mol of cresol and 0.5 mol of NaOH. While maintaining the liquid temperature of the solution at 65°–70° C., 0.5 mol of diethyl sulfate was added dropwise to the solution under vigorous agitation over a period of 15–20 minutes. After addition of the diethyl sulfate, the liquid mixture was stirred under reflux for about 30 minutes and the oily phase thus formed was thoroughly washed with a 10% aqueous solution of NaOH and then with water, dried and subjected to distillation under reduced pressure to synthetize ethoxytoluene. An autoclave was charged with 30 g of ethoxytoluene thus prepared and given amounts of a solvent and a catalyst and an oxidation reaction was carried out in a manner similar to that described in Example 1. A result of the experiments is shown in Table 12.

were prepared from commercially available phenols having the following structural formulas A'–C' and commercially available JIS-special grade p-bromotoluene. The products obtained from the phenols A'–C' are designated as A–C, respectively.

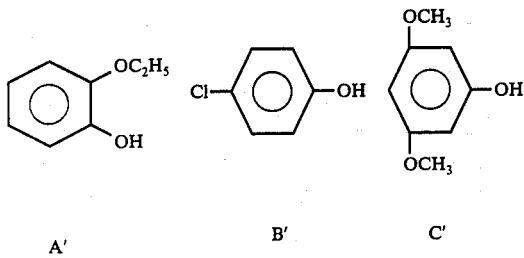

A'    B'    C'

To 40 g of the hydrocarbyloxytoluene compound

Table 12

| Exp. No. | Position of ethoxy group | Solvent [amount used]* | Catalyst [amount used]* | Reaction temp (°C) | Pressure of oxygen (kg/cm²) | Reaction time (sec) | Reaction rate (%) | Rate of selection to aldehyde (mol %) |
|---|---|---|---|---|---|---|---|---|
| 12-1 | para | Acetic anhydride[5] | Co(AcO)₂ . 4Aq[0.2] | 155–170 | 20 | 250 | 63.2 | 56.7 |
| 12-2 | para | Acetic acid[10] | Mn(AcO₂ . 4Aq[0.3] | 160–168 | 20 | 176 | 47.1 | 31.9 |
| 12-3 | meta | Acetic acid[10] | Co(AcO)₂ . 4Aq[0.2] | 165–171 | 20 | 115 | 28.7 | 30.4 |
| 12-4 | para | Propionic acid[10] | Co(AcO)₂ . 4Aq[0.3] | 160–180 | 20 | 35 | 45.8 | 60.8 |
| 12-5 | ortho | Butyric acid[15] | Cr(AcO)₂ . 4Aq[0.2] Ni(AcO)₂ . 4Aq[0.2] | 165–171 | 40 | 355 | 49.3 | 18.5 |

*In terms of molar proportion to the starting material used.

EXAMPLE 18

According to the same method as described in Example 15, hydrocarbyloxytoluene compounds

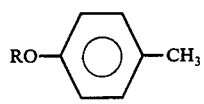

were added 100 g of acetic acid and 12.5 g of cobalt acetate Co(CH₃CO₂)₂.4H₂O. An oxidation reaction was carried out in a manner similar to that described in Example 1 under pressure of oxygen maintained at 50 kg/cm². A result of the experiments is shown in Table 13 below.

Table 13

| Starting material | Reaction temp.(° C) | Reaction time(sec) | Reaction rate (%) | Rare of selection to aldehyde(mol %) |
|---|---|---|---|---|
| A | 180–205 | 45 | 75 | 61 |
| B | 188–202 | 29 | 38 | 53 |
| C | 192–207 | 71 | 58 | 45 |

Table 13-continued

| Starting material | Reaction temp.(° C) | Reaction time(sec) | Reaction rate (%) | Rare of selection to aldehyde(mol %) |
|---|---|---|---|---|
| 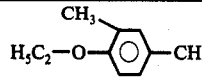 D | | | | 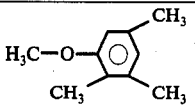 E |

Similarly, the polymethylated phenoxy compounds D and E were synthetized by conventional O-alkylation of the corresponding polymethylated phenols with diethyl sulfate and dimethyl sulfate, respectively. An oxidation reaction was carried out similarly using 200 g of acetic acid as solvent under pressure of oxygen kept at 20 kg/cm². A result of the experiments is shown in Table 14.

Table 14

| Starting material | Reaction temp.(° C) | Reaction time(sec) | Reaction rate (%) | Rate of selection to aldehyde(mol %) |
|---|---|---|---|---|
| D | 150–168 | 53 | 72.4 | 36.5* |
| E | 140–153 | 230 | 62.2 | 6.7** |

*The rate of selection to 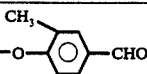

**The rate of selection to 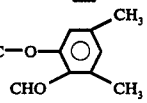

It is understood that the preceding representative examples may be varied within the scope of the present specification, both as to reactants and reaction conditions, by one skilled in the art to achieve essentially the same results.

As many apparently widely different embodiments of this invention may be made without departing from the spirit and scope thereof, it is to be understood that this invention is not limited to the specific embodiments thereof except as defined in the appended claims.

What is claimed is:

1. A process for the preparation of formylated phenoxy compounds, which comprises oxidizing a methylated phenoxy compound represented by the general formula:

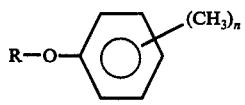

wherein R is a hydrocarbyl group with 1-20 carbon atoms selected from the group consisting of alkyl, cycloalkyl, aryl and aralkyl groups which may be substituted by, hydrocarbyloxy groups with 1-10 carbon atoms, hydrocarbyloxy carbonyl groups and halogen atoms and n is an integer of 1-5, in the liquid phase, under heat, with a pressurized oxygen-containing gas in the presence of a reaction solvent selected from the group consisting of lower fatty acids with 1-8 carbon atoms and anhydrides thereof which may be halogen-substituted, said process utilizing: a molar ratio of said reaction solvent to said methylated phenoxy compound of 0.3–18; a catalyst which is at least one salt soluble in said solvent and of a metal selected from the group consisting of cobalt, manganese, chromium and nickel; a molar ratio of said catalyst to said methylated phenoxy compound of 0.001–0.5; a molar ratio of said catalyst to said reaction solvent of 0.0001–1.0; an oxidation reaction temperature within the range of 100°–250° C.; a partial pressure of oxygen within a range of 2–100 kg/cm²; a reaction rate of conversion of less than about 90%, thereby collectively converting the methyl group of said methylated phenoxy compound into a formyl group.

2. A process according to claim 1 wherein said reaction solvent is used in an amount of 2–15 molar proportion to said methylated phenoxy compound.

3. A process according to claim 1 wherein said reaction solvent is acetic acid or acetic anhydride.

4. A process according to claim 1 wherein said lower fatty acids or anhydrides thereof are halogen-substituted ones.

5. A process according to claim 1 wherein a part of said reaction solvent is replaced by an organic solvent which is inert to the oxidation reaction.

6. A process according to claim 1 wherein said soluble salt is at least one of the group consisting of lower fatty acid salts, naphthenates and acetylacetonates.

7. A process according to claim 1 wherein said catalyst is a soluble salt of cobalt in an amount of 0.005–0.1 molar proportion to said reaction solvent.

8. A process according to claim 1 wherein said catalyst is a soluble salt of manganese in an amount of 0.01–0.05 molar proportion to said reaction solvent.

9. A process according to claim 1 wherein said catalyst is a soluble salt of nickel in an amount of 0.01–0.05 molar proportion to said reaction solvent.

10. A process according to claim 1 wherein said catalyst is a soluble salt of chromium in an amount of 0.01–0.05 molar proportion to said reaction solvent.

11. A process according to claim 1 wherein said oxidation reaction is carried out at a temperature within a range of 120°–220° C. and under a partial pressure of oxygen kept within a range 10–70 kg/cm².

12. A process according to claim 1 wherein said oxygen-containing gas is oxygen.

13. A process according to claim 1 wherein said oxygen-containing gas is air or a mixture of oxygen and air.

14. A process for the preparation of formylated phenoxy compounds characterized in that a methylated phenoxy compound is oxidized in liquid phase at a reaction temperature of 120°–200° C. with a pressurized oxygen-containing gas in which a partial pressure of oxygen is kept at 10–60 kg/cm² in the presence of acetic acid in an amount of 7–15 molar proportion to said methylated phenoxy compound and by the aid of cobalt acetate in an amount of 0.005 – 0.1 molar proportion to said acetic acid, thereby selectively converting the methyl group of said methylated phenoxy compound into formyl group.

* * * * *